United States Patent
Smith et al.

(10) Patent No.: US 9,662,351 B2
(45) Date of Patent: *May 30, 2017

(54) PLASMA AND BRAIN PHARMACOKINETICS OF PREVIOUSLY UNEXPLORED LITHIUM SALTS

(71) Applicant: University of South Florida, Tampa, FL (US)

(72) Inventors: Adam John Smith, Tampa, FL (US); R. Douglas Shytle, Largo, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/644,109

(22) Filed: Mar. 10, 2015

(65) Prior Publication Data

US 2015/0258137 A1    Sep. 17, 2015

Related U.S. Application Data

(60) Provisional application No. 61/954,397, filed on Mar. 17, 2014.

(51) Int. Cl.
*A61K 33/00* (2006.01)
*A61K 31/60* (2006.01)
*A61K 31/00* (2006.01)

(52) U.S. Cl.
CPC .............. *A61K 33/00* (2013.01); *A61K 31/00* (2013.01); *A61K 31/60* (2013.01)

(58) Field of Classification Search
CPC ........... A61K 33/00; A61K 9/00; A61K 31/60
See application file for complete search history.

(56) References Cited

U.S. PATENT DOCUMENTS 5,585,118 A * 12/1996 Stoll ...................... A61K 33/00
424/484

FOREIGN PATENT DOCUMENTS

RU            2367427     *  9/2009

OTHER PUBLICATIONS

K. Thies-Flechtner, B. Muller-Oerlinghausen, W. Seibert, A. Walther and W. Greil, Pharmacopsychiatry, "Effect of Prophylactic Treatment on Suicide Risk in Patients with Major Affective Disorders" 1996, 29, 103-107.
F. K. Goodwin, B. Fireman, G. E. Simon, E. M. Hunkeler, J. Lee and D. Revicki, "Suicide Risk in Bipolar Disorder During Treatment with Lithium and Divalproex"; JAMA, J. Am. Med. Assoc., 2003, 290, 1467-1473.
A. Cipriani, K. Hawton, S. Stockton and J. R. Geddes, "Lithium in the prevention of suicide in mood disorders: updated systematic review and meta-analysis" BMJ [Br. Med. J.], 2013, 346, f3646.
T. Fukumoto, S. Morinobu, Y. Okamoto, A. Kagaya and S. Yamawaki, Psychopharmacology, "Chronic lithium treatment increases the expression of brain-derived neurotrophic factor in the rat brain" 2001, 158, 100-106.
T. Leyhe, G. W. Eschweiler, E. Stransky, T. Gasser, P. Annas, H. Basun and C. Laske, J. "Increase of BDNF Serum Concentration in Lithium Treated Patients with Early Alzheimer's Disease" Alzheimer's Dis., 2009, 16, 649-656.
C. J. Yuskaitis and R. S. Jope, Cell. Signalling, "Glycogen synthase kinase-3 regulates microglial migration, inflammation, and inflammation-induced neurotoxicity" 2009, 21, 264-273.
A. J. Smith, S. H. Kim, N. K. Duggirala, J. Jin, L. Wojtas, J. Ehrhart, B. Giunta, J. Tan, M. J. Zaworotko and R. D. Shytle, Mol. Pharm., "Improving Lithium Therapeutics by Crystal Engineering of Novel Ionic Cocrystals" 2013, 10, 4728-4738.
P. S. Klein and D. A. Melton, "A molecular mechanism for the effect of lithium on development" Proc. Natl. Acad. Sci. U. S. A., 1996, 93, 8455-8459.
J. H. Allison and M. A. Stewart, Nature New Biol., 1971, 233, 267-268.
S. J. Pollack, J. R. Atack, M. R. Knowles, G. McAllister, C. I. Ragan, R. Baker, S. R. Fletcher, L. L. Iversen and H. B. Broughton, Proc. Natl. Acad. Sci. U. S. A., "Mechanism of inositol monophosphatase, the putative target of lithium therapy" 1994, 91, 5766-5770.
N. Singh, A. C. Halliday, J. M. Thomas, O. V. Kuznetsova, R. Baldwin, E. C. Woon, P. K. Aley, I. Antoniadou, T. Sharp, S. R. Vasudevan and G. C. Churchill, Nat. Commun., "A safe lithium mimetic for bipolar disorder" 2013, 4, 1332.
T. D. Gould and H. K. Manji, Neuropsychopharmacology, "Glycogen Synthase Kinase-3: a Putative Molecular Target for Lithium Mimetic Drugs" 2005, 30, 1223-1237.

(Continued)

*Primary Examiner* — Sarah Pihonak
*Assistant Examiner* — Jason A Deck
(74) *Attorney, Agent, or Firm* — Thomas | Horstemeyer, LLP

(57) ABSTRACT

Despite its narrow therapeutic window, lithium is regarded as the gold standard comparator and benchmark treatment for mania. Attempts to find new drugs with similar therapeutic activities have yielded new chemical entities. However, these new drugs have yet to match the many bioactivities attributable to lithium's efficacy for the treatment of neuropsychiatric diseases. Consequently, an intense effort for re-engineering lithium therapeutics using crystal engineering is underway. The evaluation of pharmacokinetics of previously unexplored lithium salts with organic anions (i.e. lithium salicylate) has found that these lithium salts exhibit profoundly different pharmacokinetics compared to the more common FDA approved salt, lithium carbonate, in rats. Remarkably, lithium salicylate produced elevated blood and brain levels of lithium beyond 48 hours post-dose without the sharp peak that contributes to the toxicity problems of current lithium therapeutics.

6 Claims, 2 Drawing Sheets

(56) References Cited

OTHER PUBLICATIONS

D. Braga, F. Grepioni, L. Maini, D. Capucci, S. Nanna, J. Wouters, L. Aerts and L. Quere, Chem. Commun., "Mechanochemistry: fundamentals and applications in synthesis" 2012, 48, 8219-8221.

J. Wouters, F. Grepioni, D. Braga, R. M. Kaminski, S. Rome, L. Aerts and L. Quere, CrystEngComm, "Novel pharmaceutical compositions through co-crystallization of racetams and Li+ salts" 2013, 15, 8898-8902.

U.S. Food and Drug Administration, Guidance for Industry: Regulatory Classification of Pharmaceutical Co-Crystals, Center for Drug Evaluation and Research, Silver Spring, U.S., Apr. 2013.

D. F. Smith, Br. J. Pharmacol., "Lithium Orotate, Carbonate and Chloride: Pharmacokinetics, Polydipsia and Polyuria in Rats" 1976, 56, 399-402.

U. Groth, W. Prellwitz and E. Jahnchen, Clin. Pharmacol. Ther., "Estimation of pharmacokinetic parameters of lithium from saliva and urine" 1974, 16, 490-498.

E. M. Trautner, R. Morris, C. H. Noack and S. Gershon, Med. J. Aust., "The excretion and retention of ingested lithium and its effect on the ionic balance of man" 1955, 42, 280-291.

S. Lippmann and R. Evans, Hospital and Community Psychiatry, "A comparison of Three Types of Lithium Release Preparations" 1983, 34, 113-114.

J. Emami, N. Tavakoli and A. Movahedian, J. Pharm. Pharm. Sci., "Formulation of Sustained release Lithium Carbonate Matrix Tablets: Influence of hydrophilic materials on the release rate and in vitro-in vivo evaluation" 2004, 7, 338-344.

B. Hille, J. Gen. Physiol., "The Permeability of the Sodium Channel to Metal Cations in Myelinated Nerve" 1972, 59, 637-658.

R. J. Baldessarini, L. Tondo and J. Hennen, Ann. N. Y. Acad. Sci., "Treating the Suicidal Patient with Bipolar Disorder Reducing Suicide Risk with Lithium" 2001, 932, 24-38; discussion 39-43.

O. Almarsson, M. L. Peterson and M. Zaworotko, Pharm. Pat. Anal., "The A to Z of pharmaceutical cocrystals: a decade of fast-moving new science and patents" 2012, 1, 313-327.

Adam J. Smith, Seol-Hee Kim, Jun Tan, Kevin B. Sneed, Paul R. Sanberg, Cesar V. Borlongan, and R. Douglas Shytle, RSC Adv., "Plasma and brain pharmacokinetics of previously unexplored lithium salts" 2014, 4, 12362.

\* cited by examiner

PLASMA AND BRAIN PHARMACOKINETICS OF PREVIOUSLY UNEXPLORED LITHIUM SALTS

This application claims priority to U.S. Provisional Application Ser. No. 61/954,397, filed Mar. 17, 2014, which is incorporated herein by reference in its entirety.

The invention relates generally to the field of medicine, and specifically, to treatment of neurological disorders.

One of the oldest psychiatric drugs in existence remains heavily utilized by clinicians today despite intense marketing of newer alternative drugs still under patent protection. This is because lithium has numerous bioactivities that remain unmatched by the alternatives. For example, lithium is the only drug that has consistently reduced suicidality in patients with neuropsychiatric disorders [1-3]. It also exerts neuroprotective effects by increasing BDNF [4,5] and attenuating the release of several inflammatory cytokines from activated microglia [6,7]. Perhaps the most highly studied bioactivities of lithium are GSK-3β inhibition [8] and inositol monophosphatase (IMPase) inhibition leading to cerebral inositol depletion [9,10]. These bioactivities have been widely regarded as the primary mechanisms of lithium therapy for its FDA-approved indication.

Recently, there have been efforts to find a lithium mimetic with improved safety [11,12]. The use of the term "lithium mimetic" is somewhat misleading since none of these new chemical entities has matched lithium's polypharmacological mechanisms of action for the treatment of neuropsychiatric diseases. In particular, lithium therapeutics are deemed the gold standard for treatment of mania, thus optimizing their safety and efficacy should have wide-ranging clinical applications.

Alternatively, others have used crystal engineering techniques to re-engineer lithium therapeutics by creating novel ionic cocrystals of lithium salts [7,13,14]. Arguably, cocrystallization represents a low risk, low cost approach with the most potential for achieving the desired therapeutic outcome for many reasons. For example, the active pharmaceutical ingredient (API) in this crystal engineering approach remains lithium, which is already FDA-approved with a long history of use in medicine. In addition, the FDA has just issued a guidance for industry regarding the regulation of pharmaceutical cocrystals that includes an expedited pathway for their approval [15]. Thus, the cost to bring a lithium cocrystal to market will likely be significantly lower than that of a new drug.

An important step in the crystal engineering of ionic cocrystals of lithium is the selection of the most appropriate parent lithium salt. One consideration that has already been identified is that the anion of the lithium salt should be pharmaceutically acceptable [7]. However, another important factor is pharmacokinetics. Often, lithium salts are assumed to dissociate following oral administration leading to very similar plasma and brain levels of lithium. In fact, one study compared lithium carbonate, lithium chloride, and lithium orotate in rats [16]. Further research showed no differences in the uptake, distribution, and excretion of the lithium ion. Still, due to the complex nature of the pharmacokinetics of multi-component materials, the evaluation of the plasma and brain pharmacokinetics of a previously unexplored salt of lithium, lithium salicylate, seemed to be a good candidate for crystal engineering endeavors. Research has proven that an unexpected pharmacokinetic difference is exhibited by this previously unexplored lithium salt in rats compared with previously-explored lithium salts. That lithium salicylate produced steady plasma lithium levels out to 48 hours while attenuating the spike associated with the toxic side effects of current lithium therapeutics is significant to crystal engineering strategies for improving the safety and efficacy of lithium therapy.

Accordingly, what is needed is novel treatment of mania using lithium salicylate. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF DESCRIPTION OF THE DRAWINGS

FIG. 1A illustrates plasma levels of lithium following administration of lithium salicylate. FIG. 1B illustrates brain levels of lithium following administration of lithium salicylate. Lithium measurements are plotted as mean±SEM ($*P<0.05$, $P<0.01$, $*P<0.001$).

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention is directed to a method of treating of neuropsychiatric diseases using lithium salicylate. Lithium salicylate was recently unexplored and research has shown that this lithium salt exhibits profoundly different pharmacokinetics compared to the more common FDA approved salt, lithium carbonate, in rats. Remarkably, lithium salicylate produced elevated plasma and brain levels of lithium beyond 48 hours post-dose without the sharp peak that contributes to the toxicity problems of current lithium therapeutics.

EXPERIMENTAL RESULTS: LITHIUM PHARMACOKINETICS

Figure 1A:
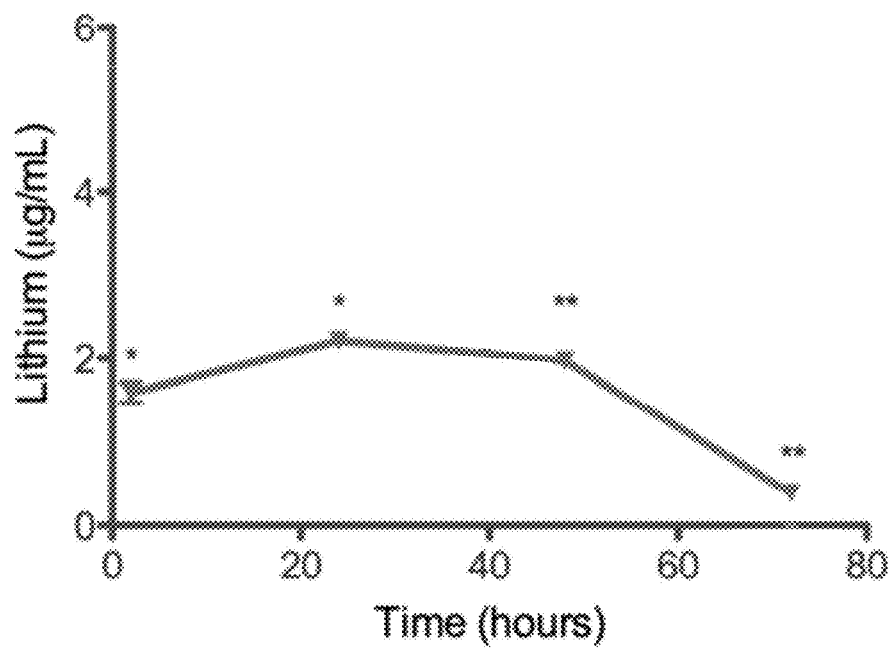
FIGS. 1A and 1B are graphs of Pharmacokinetic curves.
Figure 1B:
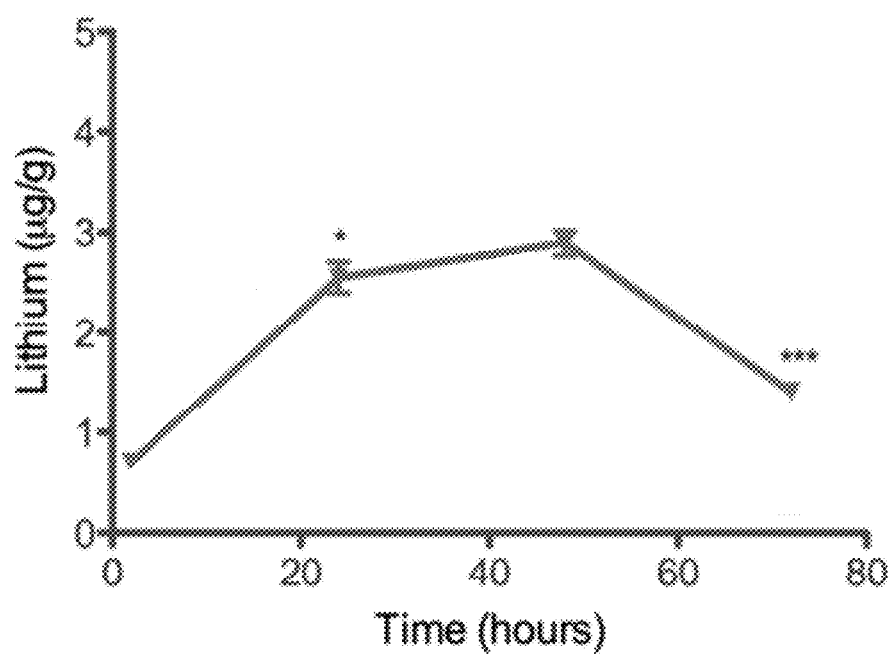

Male Sprague Dawley rats weighing 200-250 grams were dosed via oral gavage with 4 meq. $Kg^{-1}$ elemental lithium as lithium salicylate dissolved in deionized water (n =3 per time point per lithium salt). Blood and brain were collected and lithium was measured using atomic absorption spectroscopy (AAS). Plasma and brain lithium measurements are plotted as mean±SEM in FIGS. 1A and 1B, respectively.

Lithium salicylate produced elevated lithium plasma levels through the first 48 hours and was eliminated slowly. Interestingly, the lithium salicylate formulation produced elevated brain levels only at 24 and 48 hours post-dose. Table 1 shows some pertinent pharmacokinetic parameters in the experiment. However, these estimates should be used as preliminary indicators since only four carefully selected time points were utilized to limit the use of animals as much as possible. Due to the utilization of the same experimental protocol and time points for the pharmacokinetics study as previously used by Smith et al. for lithium carbonate,[7] the determination of the relative bioavailability ($F_{rel}$) of lithium salicylate compared to lithium carbonate (Table 1) was possible. The relative bioavailability of lithium salicylate was lower than lithium carbonate. The plasma and brain $F_{rel}$ of lithium salicylate was 0.35 and 0.54, respectively.

TABLE 1

Pharmacokinetic Parameters

| | Lithium Salicylate | |
| --- | --- | --- |
| | Plasma | Brain |
| $T_{MAX}$ (hour) | 24 ± 0.0 | 48 ± 0.0 |
| $C_{MAX}$ (µg h $mL^{-1}$ or µg $g^{-1}$) | 2.21 ± 0.10 | 2.89 ± 0.13 |
| $AUC_{(0-72)}$ (µg h $mL^{-1}$ or µg $g^{-1}$) | 121.8 ± 5.71 | 153.1 ± 7.66 |
| $F_{rel}$ (vs. lithium carbonate) | 0.35 | 0.54 |

There is a large disparity in regards to comparative studies of the pharmacokinetics of lithium salts in the peer-reviewed literature. Until now, only lithium chloride, carbonate, and orotate have been subjected to these types of studies [16]. The present study represents the first in vivo pharmacokinetic assessment of lithium salicylate. Because lithium salicylate is considered pharmaceutically acceptable and amenable for cocrystallization using crystal engineering techniques [7], such pharmacokinetic data will be critical in advancing lithium therapeutics.

Interestingly, lithium salicylate exhibited an unexpected pharmacokinetic profile that is unlike any other lithium salt reported in the literature to date. The known toxicity issues of FDA approved lithium salts could be exacerbated by their pharmacokinetics given its narrow therapeutic window. As previously reported, lithium carbonate peaks rapidly and is eliminated within 48 hours [7]. Comparatively, the lithium salt in the present study underperformed lithium carbonate from bioavailability standpoints. However, given that oral bioavailability is not a problem with lithium therapeutics [17,18] it is not anticipated that this discrepancy will disqualify either of these salts for development as drugs. In fact, the plateau plasma levels observed in this study of lithium salicylate could improve the safety of lithium therapy and, consequently, improve patient compliance. This is supported by previous investigators who suggested that an ideal lithium preparation would attenuate high blood level peaks and exhibit gradually declining blood concentrations [19]. Encouragingly, this is precisely the pharmacokinetic profile that was produced by lithium salicylate in the study (see FIGS. 1A and 1B). Previous attempts at formulating proprietary controlled release lithium therapeutics have been somewhat successful at prolonging lithium plasma levels [20]. Nonetheless, the lithium salicylate formulation still produced the initial plasma spike attributable to toxicity problems observed in lithium therapy. It was also discovered that lithium salicylate produced comparatively lower plasma lithium exposure than other lithium salts (e.g. lithium lactate), but lithium salicylate produced better brain exposure. Thus, biodistribution also appears to be affected by the choice of anion.

Indeed, these pharmacokinetic differences were unexpected since lithium salicylate was administered fully dissolved in an aqueous solution, eliminating the possibility of solubility-mediated effects. This would lead one to predict that the lithium pharmacokinetics would be similar for lithium salicylate and other lithium salts (e.g. lithium lactate). Since that was not the case, it is hypothesized that the observed "plateau effect" and modulated brain biodistribution of lithium as lithium salicylate is likely due to absorption, distribution, metabolism, and/or elimination (ADME) effects from the salicylate anion. The precise mechanism for this is unclear. However, this could be due to the chemical modification of the physiological transporter(s) of lithium ions in vivo. For example, sodium ion transporters have similar permeability for both sodium and lithium ions [21]. It is feasible that salicylate chemically modifies the sodium ion transporter, changing its permeability.

Because lithium is so effective at treating neuropsychiatric diseases such as bipolar disorder and suicidality [1,22,23] it is still used despite known toxicity issues that require frequent blood monitoring by a clinician. Finding a new molecule that is a true "lithium mimetic" is probably a lost cause and recognize that crystal engineering approaches like cocrystallization could solve the toxicity issues. The preliminary data presented here demonstrates that some currently available but understudied lithium salts (e.g. lithium salicylate) may also solve the toxicity issues of conventional lithium salts (e.g. lithium carbonate and lithium citrate). However, developing new lithium salts as drugs would require significant investment from a pharmaceutical company without composition of matter patent protection. Cocrystals are patentable [24], which improves the likelihood of realizing a good return on the investment required to develop them as a new drug. Moreover, cocrystals of lithium salts might also offer improved efficacy since the coformers can be rationally selected to be synergistic as discussed in recent crystal engineering efforts [13,14].

EXAMPLE

Figure 2:
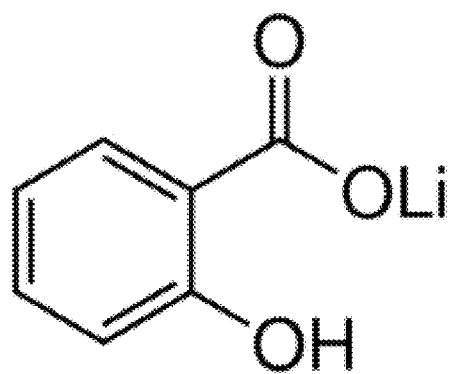
FIG. 2 is a representation of the chemical structure of lithium salicylate.

Reagents and Materials. Lithium salicylate (≥98% purity) was purchased from Sigma-Aldrich Corporation (St. Louis, Mo., USA) and used as such without further purification. The chemical structure of lithium salicylate is shown in FIG. 2. Lithium salicylate was characterized using powder X-ray diffraction. This data is included as ESI.

Pharmacokinetics Studies. Previously described methodologies were used for the pharmacokinetics studies [7]. Male Sprague Dawley rats weighing 200-250 grams were purchased from Harlan (Harlan Sprague Dawley Inc., Indianapolis, Ind.). The animals were housed at the Moffitt Cancer Center vivarium (Tampa, Fla.) with a 12-hour light-dark cycle. The rats were allowed to acclimate for a period of one week before any experiments are carried out. All experiments were conducted in accordance with USF IACUC approved protocols. They were allowed free access to food and water throughout the experiment. The rats were dosed via oral gavage with 4 meq. kg$^{-1}$ elemental lithium as lithium salicylate dissolved in deionized water. Animals in each treatment group were euthanized at 2, 24, 48, and 72 hours (n=3 per time point per lithium salt) and blood was collected by cardiac puncture and carefully perfused with a pressure controlled pump to maintain microvasculature integrity before removing brain tissue. Blood was centrifuged at 1600×g at room temperature for 10 minutes and plasma was separated. A 500 mL aliquot was diluted 10 fold in a 5% TCA and 10% isopropyl alcohol (IPA) solution, vortexed and allowed to sit for 10 minutes in order to precipitate proteins. These aliquots were centrifuged at 3000×g for 30 minutes and the supernatant was transferred to clean tubes prior to measuring lithium content using atomic absorption spectroscopy (AAS). Brains were rinsed with PBS, weighed, and an equal volume of concentrated HNO3 was added. The brains were heated in this nitric acid solution for 1 hour, allowed to cool to room temperature, then centrifuged at 3000×g for 1 hour. The supernatant was removed and diluted 10 fold in 10% IPA prior to measuring lithium content using AAS (Shimadzu AA-6200). Peak height measurements were carried out referring to values obtained for standards of known concentrations. Lithium measurements were plotted using GraphPad PRISM software (GraphPad Software, Inc.) as mean±SEM in FIG. 1. Two tailed t-tests were used to assess the statistical significance at each time point for the pharmacokinetic curves. The criterion for rejection of the null hypothesis was P<0.05. Phoenix WinNonlin® Version 6.3 (Pharsight Corporation, Mountain View, Calif.) was used to conduct a non-compartmental analysis of the pharmacokinetic data and generate the pharmacokinetic parameters in Table 1 as mean±SEM. The reported parameters include $C_{MAX}$, $T_{MAX}$, area under curve (AUC), and relative bioavailability ($F_{rel}$).

REFERENCES

1. K. Thies-Flechtner, B. Muller-Oerlinghausen, W. Seibert, A. Walther and W. Greil, Pharmacopsychiatry, 1996, 29, 103-107.
2. F. K. Goodwin, B. Fireman, G. E. Simon, E. M. Hunkeler, J. Lee and D. Revicki, JAMA, J. Am. Med. Assoc., 2003, 290, 1467-1473.
3. A. Cipriani, K. Hawton, S. Stockton and J. R. Geddes, BMJ [Br. Med. J.], 2013, 346, f3646.
4. T. Fukumoto, S. Morinobu, Y. Okamoto, A. Kagaya and S. Yamawaki, Psychopharmacology, 2001, 158, 100-106.
5. T. Leyhe, G. W. Eschweiler, E. Stransky, T. Gasser, P. Annas, H. Basun and C. Laske, J. Alzheimer's Dis., 2009, 16, 649-656.
6. C. J. Yuskaitis and R. S. Jope, Cell. Signalling, 2009, 21, 264-273.
7. A. J. Smith, S. H. Kim, N. K. Duggirala, J. Jin, L. Wojtas, J. Ehrhart, B. Giunta, J. Tan, M. J. Zaworotko and R. D. Shytle, Mol. Pharm., 2013, 10, 4728-4738.
8. P. S. Klein and D. A. Melton, Proc. Natl. Acad. Sci. U.S.A., 1996, 93, 8455-8459.
9. J. H. Allison and M. A. Stewart, Nature New Biol., 1971, 233, 267-268.
10. S. J. Pollack, J. R. Atack, M. R. Knowles, G. McAllister, C. I. Ragan, R. Baker, S. R. Fletcher, L. L. Iversen and H. B. Broughton, Proc. Natl. Acad. Sci. U.S.A., 1994, 91, 5766-5770.
11. N. Singh, A. C. Halliday, J. M. Thomas, O. V. Kuznetsova, R. Baldwin, E. C. Woon, P. K. Aley, I. Antoniadou, T. Sharp, S. R. Vasudevan and G. C. Churchill, Nat. Commun., 2013, 4, 1332.
12. T. D. Gould and H. K. Manji, Neuropsychopharmacology, 2005, 30, 1223-1237.
13. D. Braga, F. Grepioni, L. Maini, D. Capucci, S. Nanna, J. Wouters, L. Aerts and L. Quere, Chem. Commun., 2012, 48, 8219-8221.
14. J. Wouters, F. Grepioni, D. Braga, R. M. Kaminski, S. Rome, L. Aerts and L. Quere, CrystEngComm, 2013, 15, 8898-8902.
15. U.S. Food and Drug Administration, Guidance for Industry: Regulatory Classification of Pharmaceutical Co-Crystals, Center for Drug Evaluation and Research, Silver Spring, U.S., April 2013.
16. D. F. Smith, Br. J. Pharmacol., 1976, 56, 399-402.
17. U. Groth, W. Prellwitz and E. Jahnchen, Clin. Pharmacol. Ther., 1974, 16, 490-498.
18. E. M. Trautner, R. Morris, C. H. Noack and S. Gershon, Med. J. Aust., 1955, 42, 280-291.
19. S. Lippmann and R. Evans, Hospital and Community Psychiatry, 1983, 34, 113-114.
20. J. Emami, N. Tavakoli and A. Movahedian, J. Pharm. Pharm. Sci., 2004, 7, 338-344.
21. B. Hille, J. Gen. Physiol., 1972, 59, 637-658.
22. R. J. Baldessarini, L. Tondo and J. Hennen, Ann. N. Y. Acad. Sci., 2001, 932, 24-38; discussion 39-43.
23. F. K. Goodwin, B. Fireman, G. E. Simon, E. M. Hunkeler, J. Lee and D. Revicki, JAMA, J. Am. Med. Assoc., 2003, 290, 1467-1473.
24. O. Almarsson, M. L. Peterson and M. Zaworotko, Pharm. Pat. Anal., 2012, 1, 313-327.
25. Adam J. Smith, Seol-Hee Kim, Jun Tan, Kevin B. Sneed, Paul R. Sanberg, Cesar V. Borlongan, and R. Douglas Shytle, RSC Adv., 2014, 4, 12362.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating a neuropsychiatric disease, in a human or animal subject, wherein the neuropsychiatric disease is at least one of bipolar disorder or suicidality, the method comprising orally administering a composition comprising a therapeutically-effective amount of lithium salicylate to said subject.

2. The method of claim 1 wherein the method comprises gradually increasing the plasma concentration of lithium of the subject over a first period of about 0 to 24 hours following a first administration of the lithium salicylate composition to said subject.

3. The method of claim 2, wherein the method further comprises gradually decreasing the plasma concentration of lithium of the subject over a second period of at least about 24 to 48 hours following a first administration of the lithium salicylate composition to said subject.

4. The method of claim 3, wherein the plasma concentration of lithium of the subject returns to approximately a pre-administration baseline level more than 48 hours following a first administration of the lithium salicylate composition.

5. The method of claim 1 wherein the method comprises gradually increasing the brain concentration of lithium of the subject over a first period of about 0 to at least about 24 hours following a first administration of the lithium salicylate composition to said subject.

6. The method of claim 1 wherein the lithium salicylate composition is an aqueous solution.

\* \* \* \* \*